United States Patent [19]

Bosnjakovic

[11] Patent Number: 4,700,074
[45] Date of Patent: Oct. 13, 1987

[54] SCINTILLATION CRYSTAL DEVICE AND SCINTILLATION CAMERA INCORPORATING SUCH DEVICE

[76] Inventor: Vladimir B. Bosnjakovic, Prote Mateje 39, 11000 Belgrade, Yugoslavia

[21] Appl. No.: 887,500

[22] Filed: Jul. 21, 1986

[30] Foreign Application Priority Data

May 21, 1986 [YU] Yugoslavia .............................. 845/86

[51] Int. Cl.⁴ ........................ G01T 1/202; G01T 1/164
[52] U.S. Cl. .................................. 250/363 S; 250/368; 250/483.1; 250/486.1
[58] Field of Search ...................... 250/486.1, 368, 367, 250/363 SR, 483.1

[56] References Cited

U.S. PATENT DOCUMENTS 4,415,808  11/1983  Cusano et al. ...................... 250/367
4,560,882  12/1985  Barbaric et al. ..................... 250/367

FOREIGN PATENT DOCUMENTS

3001103  7/1981  Fed. Rep. of Germany ...... 250/366

*Primary Examiner*—Carolyn E. Fields
*Attorney, Agent, or Firm*—Mark H. Jay; John Francis Moran

[57] ABSTRACT

In order to match the trends and demands of modern nuclear medicine, a new scintillation camera head is designed, which features a new crystal-light guide-collimator unit for a single crystal scintillation camera. The effective crystal thickness is increased by crystal teeth designed as quadrilateral truncated crystal pyramids. The basis of each of these teeth is settled on top of a crystal plate of conventional thickness. The vertical axis of each of the teeth is aligned with the vertical axis of a particular collimator channel. Thus, the total number of crystal pyramids equals the number of (preferably squared) collimator holes. The space between the crystal pyramids is "filled" with an appropriate light guide material such as window glass. The crystal pyramid side is shaped, i.e. angled, according to the direction of the highest (gamma) photon energy the camera is designed for, after penetrating through the upper (close to crystal) portion of the collimator septum for a length equaling $2\mu^{-1}$; where $\mu$ is the linear absorption coefficient for the (gamma) photon energy in the particular collimator material, such as tantalum (Ta). Thus, the increased crystal thickness is made effective only for photons coming from the "proper" collimator channel, while the absorption of photons from surrounding channels is basically prevented. Theoretical predictions indicate that about 90% of them will take their primary (and secondary) interactions with the light guide and not with the crystal material.

13 Claims, 15 Drawing Figures

|  | Density | Refr. index |
|---|---|---|
| NaI : | 3,667 | 1,7745 |
| SiO₂-Quartz : | 2,660 | 1,553 |

SCINTILLATION CRYSTAL DEVICE AND SCINTILLATION CAMERA INCORPORATING SUCH DEVICE

BACKGROUND OF THE INVENTION

1. Field of the Invention

This invention relates to a novel and improved scintillation crystal device. It also relates to a novel and improved scintillation camera incorporating such crystal device. Generally speaking, this invention relates to the field of nuclear medicine.

2. Description of the Prior Art

The trends in modern nuclear medicine go towards the use of new radionuclides, radiopharmaceuticals and imaging techniques (such as with 81 m-Kr, 111-In, 195 m-Au, 75-Se, 67-Ga, 131-I—labelled antibodies), "first pass" cardiology studies, planar studies with positron emitters, single photon emission computerized tomography (SPECT), and positron emission tomography (PET). The contemporary single crystal scintillation cameras (SCs) of the Anger type (see e.g. U.S. Pat. No. 3,011,057 to Anger) with reduced crystal thickness, due to improvements made in the domain of distortion correction, as far as linearity and uniformity are concerned (see e.g. U.S. Pat. No. 3,745,345 to Muehllehner and U.S. Pat. No. 4,298,944 to Stoub et al.) achieve fine intrinsic spatial resolution. They are quite acceptable for static and slow-dynamic planar imaging with low energy single photon emitting tracers having energies up to 140 KeV (such as 133-Xe, 201-Tl, and the most widespread one, 99 m-Tc). However, their potentials in "first pass" nuclear cardiology studies, in efficient detection of the above listed medium energy gamma emitting radionuclides, as well as in SPECT with rotating SC heads and detection of positron emitters (planar and tomographic with dual head cameras) are limited. Recently, this problem was addressed in an article entitled "Improved Intrinsic Resolution: Does It Make a Difference?" by Hoffer et al. in J. Nucl. Med. 25, 230 (1984).

Multi-crystal cameras (MCs) (see e.g. Bender and Blau: "The Autofluoroscope"; Nucleonics 21, 10, 52 (1963)) are sensitive enough and, therefore, advantageous for high counting rate dynamic studies and efficient detection of medium and high energy photons. The disadvantage of MCs is that they have poor spatial and energy resolution.

Collimators of various configurations for scintillation cameras are disclosed in U.S. Pat. Nos. 3,921,000, 3,943,366 and 4,057,726, which are incorporated herein by reference.

SUMMARY OF THE INVENTION

The invention is based on the following consideration:

In order to meet the requirements of modern nuclear medicine, a new design concept of the physical parts, i.e. of the crystal-light guide-collimator complex or unit of a single crystal SC, is to be conceived to achieve an optimum trade-off between the essential properties of single-crystal and multi-crystal cameras. In other words, by sacrificing in spatial resolution up to a tolerant extent in a single crystal SC, the temporal resolution and efficiency for higher energy photons of a MC may be approached.

1. Objects

An object of this invention is to provide a scintillation crystal arrangement for use in conjunction with a single crystal scintillation camera, which arrangement yields an improved temporal resolution and an improved efficiency for photons (gamma quanta, positrons, etc.) of relatively high energy, such as 360 KeV.

Another object of this invention is to provide a scintillation camera incorporating such crystal.

2. Summary

According to this invention, a scintillation crystal arrangement comprises:

(a) a crystal base having a first end for receiving radiation, and a second end opposite to said first end; and (b) a plurality of crystal teeth in the form of truncated pyramids, said teeth being arranged on said second end of said crystal base.

In a preferred embodiment, the pyramids have a quadrilateral configuration.

According to this invention, a scintillation camera comprises:

(a) a collimator having a plurality of parallel channels for receiving and for transmitting radiation therethrough, (b) a predetermined number of photomultipliers arranged in an array, and (c) a scintillation crystal device disposed between said collimator and said photomultiplier array, wherein said arrangement contains (c1) a crystal base having a first end for receiving radiation transmitted through said collimator channels, and a second end opposite to said first end; and (c2) a plurality of crystal teeth in the form of truncated pyramids having parallel longitudinal axes, said teeth being arranged on said second end of said crystal base such that said longitudinal axes of said pyramids are aligned with the longitudinal axes of said collimator channels.

In a preferred embodiment, the collimator channels may have a squared configuration.

The foregoing and other objects, features and advantages of this invention will be apparent from a consideration of the following detailed description of preferred embodiments of the invention in conjunction with the accompanying drawings.

DESCRIPTION OF THE PREFERRED EMBODIMENTS

Figure 1:
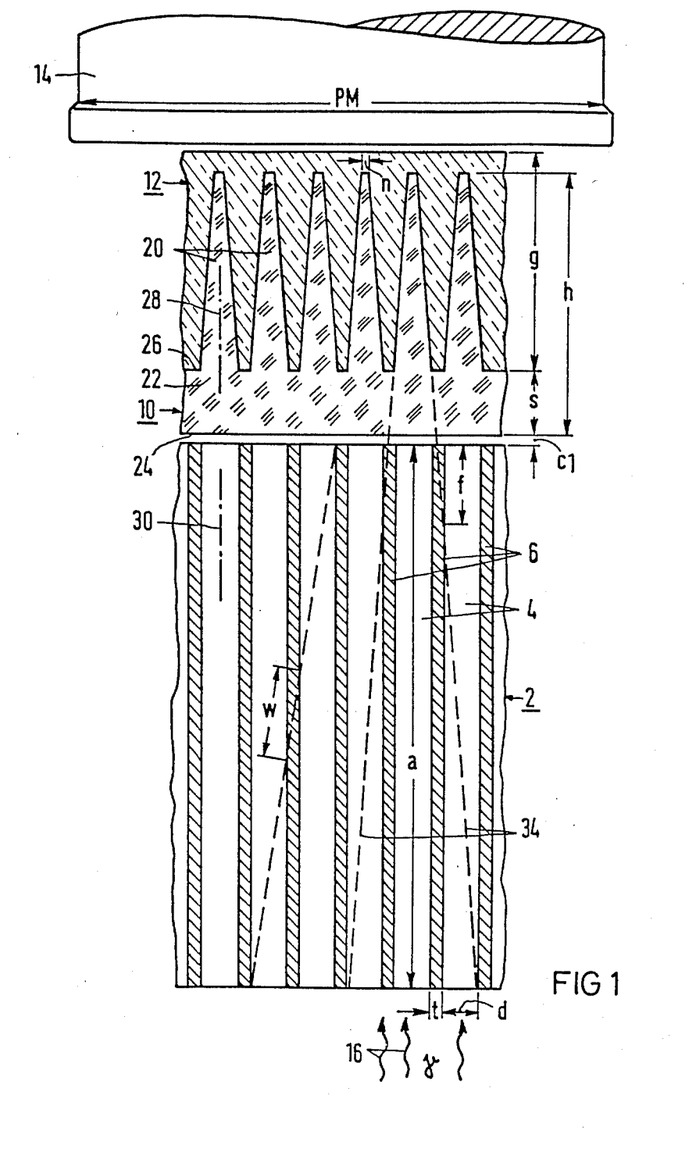
FIG. 1 illustrates the basic design concept of a detector head for a single crystal scintillation camera incorporating a scintillation crystal device in accordance with the invention.

The design concept of a scintillation crystal device according to the invention for use in a single crystal scintillation camera is shown in FIG. 1. The two-dimensional vertical cross-sectional view, which is partially broken away, depicts a collimator 2 having a plurality of parallel apertures or channels 4 which are divided from each other by septa 6, a scintillation crystal 10, a light guide 12 and a predetermined number of photomultiplier tubes arranged in an array in a conventional manner, of which only photomultiplier 14 is visible in FIG. 1. The channels 4 are designed for receiving and transmitting radiation, such as gamma radiation 16 from a patient's body. The scintillation crystal device 10, 12 includes a crystal 10 made of a material such as preferably NaI doped with Tl. It is disposed between the collimator 2 and the photomultiplier array. In particular, tube 14 may be a "two inches" photo multiplier (PM) tube.

The parameters originally given by Anger and used in the formulas throughout the theoretical presentation of this patent specification are represented in Table I:

TABLE I

| | |
|---|---|
| d | width of collimator channel 4; |
| b | distance from radioactive subject to collimator entrance (computations done for b = 10 cm); |
| c | distance from collimator exit facing the crystal 10 to central plane of the crystal (for a $\frac{1}{4}''$ thick crystal, c = 3.175+ + 0.8 = 3.975 mm; where 0.8 mm = $c_1$, the thickness of the aluminium can (not shown)); |
| k | constant, depending on collimator hole shape: for squared holes, k = 0.282; |
| a | actually measured collimator length; |
| $a_e$ | effective collimator length; |
| $\mu^{-1}$ | mean free path of a gamma ray in a particular material, where $\mu$ is the linear absorption coefficient; |
| t | thickness of collimator septum 6; |
| w | shortest distance of an unwanted path of a gamma ray transversal penetration through collimator septum 6 (in a Siemens 364 KeV collimator (for Pb), w = 2.72 $\mu^{-1}$, see Siemens leaflet, 1984). |

The essential idea of the invention as compared to the prior art is to increase the crystal thickness without serious impairment of spatial resolution. To this end, a particularly shaped crystal-light guide complex is designed, where an increase in crystal thickness (over the crystal layer of conventional thickness) is achieved by providing additional crystal pyramids or "teeth" 20 on top of a crystal base 22. The crystal base 22 has a first face or end 24 for receiving radiation transmitted through the collimator channels 4, and a second end 26 opposite to the first end 24. The crystal teeth 20 in the form of truncated pyramids have their parallel longitudinal axes 28 aligned with the longitudinal axes 30 of the collimator channels 4. Between the crystal "teeth", as well as on top of them, the material of the light guide 12 is inserted. This design increases the effective crystal thickness for high energy radiation, such as gamma photons, coming from a collimator channel 4 the axis 30 of which fits the axis 28 of a particular crystal tooth. Undesirable gamma photons coming from neighbouring collimator channels 4 will not be detected since about 90% of them will primarily interact with the light guide material 12 and not with the crystal 10.

Anger ("Instrumentation in Nuclear Medicine", Academic Press, New York (1967), p. 485) showed a significant loss of positioning resolution in a NaI crystal with its increased thickness and with a rise of gamma energy; this is due not only to the simple geometric overlapping of the "view domains" of neighbouring collimator holes or channels 4 in the crystal, but also to the possibility of multiple Compton-photoelectric interactions (which are the main contributors to the photopeak at higher gamma energies). The present effectively thicker crystal design will, by interposing the light guide material 12 between the crystal pyramids or teeth 20, prevent or at least reduce both of the afore-mentioned undesirable effects, since not only photons of primary interactions, but also most of the scattered photons will "escape" to the light-guide material without being detected. Thus, only Compton interactions followed immediately by photoelectric interactions occurring within the crystal teeth, which do not worsen the intrinsic resolution, will be detected. Practically, the intrinsic resolution for gamma energies above 140 KeV will remain as predetermined by the size of the crystal pyramids, i.e. by the present design of the collimator-crystal-light guide complex. Thus, the Anger positioning of events principle, by employing the conventional photomultiplier tube array and the decoding electronics of a single crystal scintillation camera, is made applicable with an effectively thicker crystal 10.

One of the essential characteristics of the present scintillation camera is that the design of the collimator-crystal-light guide complex is strictly interdependent. The simplest and the most practical design would be with square shaped cross-sections of the teeth 20 in the crystal-light guide complex; i.e. a preferred embodiment contains squared (quadrilateral) truncated pyramids of crystal teeth 20 positioned on top of the standard crystal plate 22 having a thickness of $\frac{1}{4}''$, with a light guide-glass window material "filling" the space between the individual crystal pyramids 20 and also covering their truncated tops. In this preferred embodiment, squared collimator channels 4 are applied, with their axes being aligned with the axes of the crystal teeth 28.

Preferably, in a camera there can be used four collimators, covering the gamma photon energy ranges of modern radionuclides, up to 360 KeV, as listed in Table II.

TABLE II

| Energy range | | Collimator | |
| (max. KeV) | Radionuclides | No. | Design |
|---|---|---|---|
| 140 | 133-Xe<br>201-Tl | 1 | Conventional |

TABLE II-continued

| Energy range (max. KeV) | Radionuclides | Collimator No. | Design |
|---|---|---|---|
| 190 | 99m-Tc 123-I 67-Cu | 2 | Especially designed |
| 270 | 81m-Kr 111-In 195m-Au 75-Se | 3 | Especially designed |
| 360 | 67-Ga 51-Cr 131-I | 4 | Especially designed |

The particular values for $\mu$, i.e. the linear absorption (attenuation) coefficient, and derived values for f, as used throughout this patent specification, are listed in Table III.

TABLE III

| Energy range (max KeV) | Material | $\mu$ (in cm$^{-1}$) | f ($2\mu^{-1}$; in mm) |
|---|---|---|---|
| 140 | NaI | 2.2 | — |
| | Pb | 23.8 | — |
| | Ta | 27.4 | 0.73 |
| 190 | NaI | 0.9 | — |
| | Pb | 10.6 | — |
| | Ta | 12.6 | 1.6 |
| 270 | NaI | 0.425 | — |
| | Pb | 4.18 | — |
| | Ta | 6.64 | 3.0 |
| 360 | NaI | 0.215 | — |
| | Pb | 2.78 | — |
| | Ta | 3.12 | 6.4 |

Now details of the scintillation crystal device and its application to a scintillation camera will be specified.

(a) Crystal-Light Guide Design

A particular camera head construction is presented in FIG. 1 with the collimator 2 designed for a maximum photon energy of 360 (364) KeV, which may be called the "basic" collimator. The collimator 2 is made of Tantalum (=Ta; density $\rho$=16.6 g/cm$^3$), which offers greater attenuation (absorption) for gamma photons than lead (=Pb), and it is needed for a particular design of the collimator-light guide-crystal complex. The parameters and dimensions of the "basic" collimator 2 illustrated in FIG. 1 are listed in Table IV:

TABLE IV

| | |
|---|---|
| a | 51 mm; |
| $a_e$ | 44.59 mm; |
| d | 3.4 mm; |
| t | 1.2 mm; |
| f | photon penetration through the upper part of collimator septum (6.41 mm; details to be given below); |
| w | 2.42 $\mu^{-1}$, or, 3.49 d/2 of Ta for 364 KeV ($\mu$ = 3.12 cm$^{-1}$; d/2 = 2.22 mm); |
| $c_1$ | aluminum can-shield (0.8 mm); |
| s | standard or conventional crystal thickness (for NaI: 6.35 mm = ¼"); |
| h | maximum crystal thickness (25.4 mm = 1"), i.e. s plus full height of crystal teeth 20; |
| g | thickness of glass window (= light guide 12), including height of glass window "inverted teeth" (21.175 mm); |
| n | width of the top of a crystal tooth (0.83 mm); |
| (s + g) | total thickness of crystal-light guide complex (27.525 mm); |
| PM | photomultiplier tube(diameter 2"). |

The photon direction is given in dashed lines 34. The above-mentioned parameters are kept the same throughout this patent specification.

In principle, the design of the crystal teeth 20 should be done in accordance with the "basic" collimator 2 designed for the highest (e.g. gamma) photon energy the scintillation camera is planned for. The reason is that the collimator septum penetration of gamma rays is the greatest at this energy, requiring the design of the sharpest angle of the sides of the crystal pyramids or teeth 20 relative to their bases; such an angle or slope would be safe enough to prevent all gamma photons of lower energies from surrounding collimator holes (due to a smaller penetration) from being undesirably absorbed.

The crystal teeth 20, with the axis 28 of each precisely fitting the axis 30 of a particular or corresponding collimator channel 4, are shaped according to gamma photon directions from surrounding collimator holes by their continuation within the crystal-light guide medium; such continued directions determine the borderlines between the crystal teeth and the light-guide material (e.g. glass window).

Figure 2A:
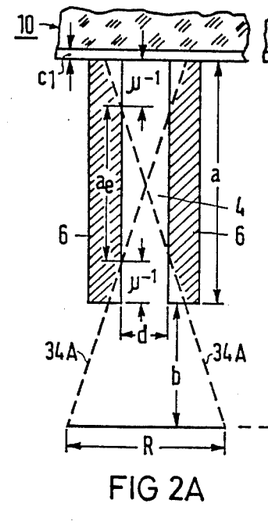
FIG. 2 illustrates a septum penetration principle used in the design of the collimator-crystal complex of FIG. 1.
Figure 2B:
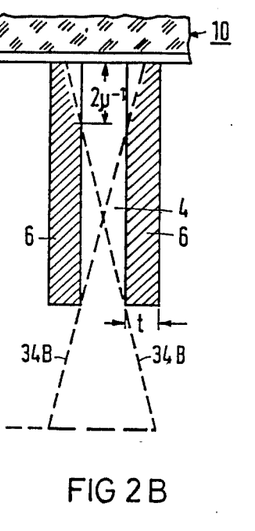

The conventional collimator design assumes that a and $a_e$ are related with each other as follows:

$$a_e = a - 2\mu^{-1}, \quad (1)$$

where $2\mu^{-1}$ represents the septum penetration factor, and $\mu$ represents the linear absorption coefficient of a particular collimator material (in this case, of Ta) for a particular photon energy (in this case, for 360 KeV); it further assumes that $2_M^{-1}$ should be split and distributed to both collimator hole ends each being given $\mu^{-1}$ of the septal penetration length, as illustrated in FIG. 2A. However, I assigned the "whole amount" of $2\mu^{-1}$ to the upper portion of the septum 6, as shown in FIG. 2B, in order to give the sharpest possible angle to the sides of the crystal pyramids or teeth 20 (relative to their bases). Such crystal teeth design minimizes the possibility of photons exiting from surrounding collimator channels 4 to produce primary or secondary interactions with the crystal material of a particular tooth 20. Then, the crucial factor f which determines the direction of a gamma photon passing through the upper (close to the crystal) portion of the collimator septum 4, is given by:

$$f = 2\mu^{-1} \quad (2)$$

The present design of the whole crystal-light guide block assumes that the crystal teeth 20 are settled in the appropriately shaped light guide recesses and that they are optionally coupled with the light guide 12 (e.g. made of window glass).

Figure 3:
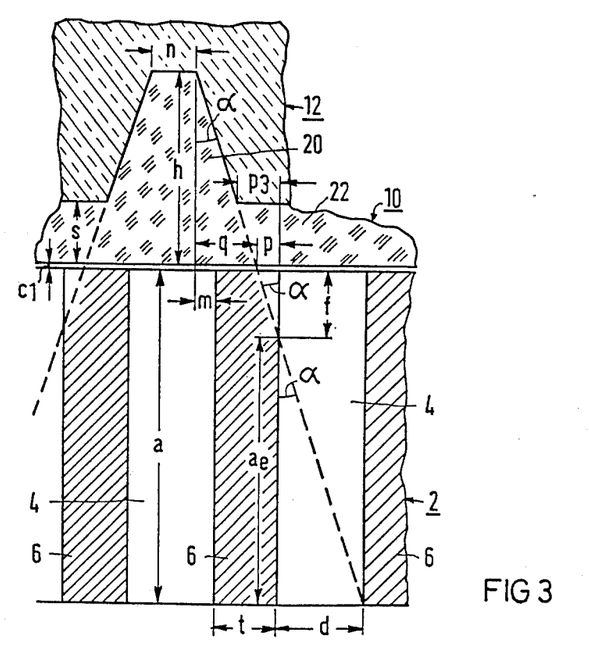
FIG. 3 shows a principle and parameters developed for the design and evaluation of the collimator-crystal-light guide complex of FIG. 1.

Important geometric relations facilitating the design of the crystal-light guide complex in accordance with a "basic" collimator 2 are given in the FIG. 3. Two collimator channels 4, one crystal tooth 20, and the design principle are illustrated. Thus, the essential collimator parameters can be expressed in terms of the following geometric relations:

$$d = 2m + n \quad (3)$$

$$t = (p+q) - m \quad (4)$$

$$a = a_e + f \quad (5)$$

where m, p, and q are factors specific for the design, as illustrated in FIG. 3.

One of the design essentials upon defining f, as pointed out, is to define the slope of a crystal tooth side, represented by $tg\gamma$, which is given by the following relations:

$$d/(a-f) = d/a_e = p/f = q/(h+c_1) = tg\gamma.$$

The maximum crystal thickness h should not equal less than 1″. Then, a specific parameter, namely the width n of a crystal tooth top which is indicative for the size of a crystal tooth volume, can be derived from the following relations:

$$m+t = p+q; \quad p = df/(a-f); \quad q = d(h+c_1)/(a-f);$$
$$n = d - 2 m;$$

and n can be calculated by the following equation:

$$n = d - 2((d(f+h+c_1)/(a-f)) - t). \quad (6)$$

It is assumed that n should not equal less than 0.8 mm. The combined parameter n, incorporating all essential parameters a, d, t, f, and h, will give a good insight into the adequacy of the crystal-light guide complex design.

(b) Collimator Design

The first step in the scintillation camera design is the design of a collimator 2 for the highest (gamma) photon energy the camera is planned for. In this embodiment, the "basic" collimator 2 is made of tantalum and is designed for 360 (364) KeV. The preliminary design is made according to characteristics of a similar collimator used with a conventional single crystal scintillation camera, in this case according to the Siemens 364 KeV collimator (Siemens leaflet, 1984). Actually, a preliminary design of my 360 KeV colimator has retained the similarity in geometric efficiency E, and geometric resolution R, to the Siemens 364 KeV collimator (equations 16 and 17 are useful), with some reduction of the length, narrowing of the channels 4 and thinning of the septa 6, which was made possible by the Ta material (equations 14 and 15 are useful). Thus, the design of two collimators for lower (gamma) energies (such as 270 and 190 KeV, see Tables II and III, also made of Ta) is "prepared", both of which have better geometric efficiencies and geometric resolutions as compared to the "basic" collimator.

Geometric efficiency E and geometric resolution R as well as minimum permissible septal thickness t are calculated according to Anger formulas:

$$E = 10^6 \cdot ((kd^2/a_e(d+t))^2 \quad (7)$$

(E being a dimensionless relative number), $$R = d(a_e + b + c)/a_e \quad (8)$$

(R being given in terms of mm of the "full width at half maximum"-FWHM, at a 10 cm distance), $$t = 2dw/(a-w), \quad (9)$$

where the parameters used are defined in Table I, and wherein $a_e$ is given by equation (1).

Typical values of the "basic" collimator design for a, ($a_e$), d, t, k, b and c are listed in Tables I and IV; from equations (7) and (8) the values for E and R for the "basic" collimator (360 KeV, Ta) are derived to be 254 (relative number) and 11.3 mm (FWHM at 10 cm), respectively. The rest of the "basic" collimator design dependent parameter values, including the value for f, for the parameter n, and predetermined values for s, h and g are given in Table IV.

Figure 4:
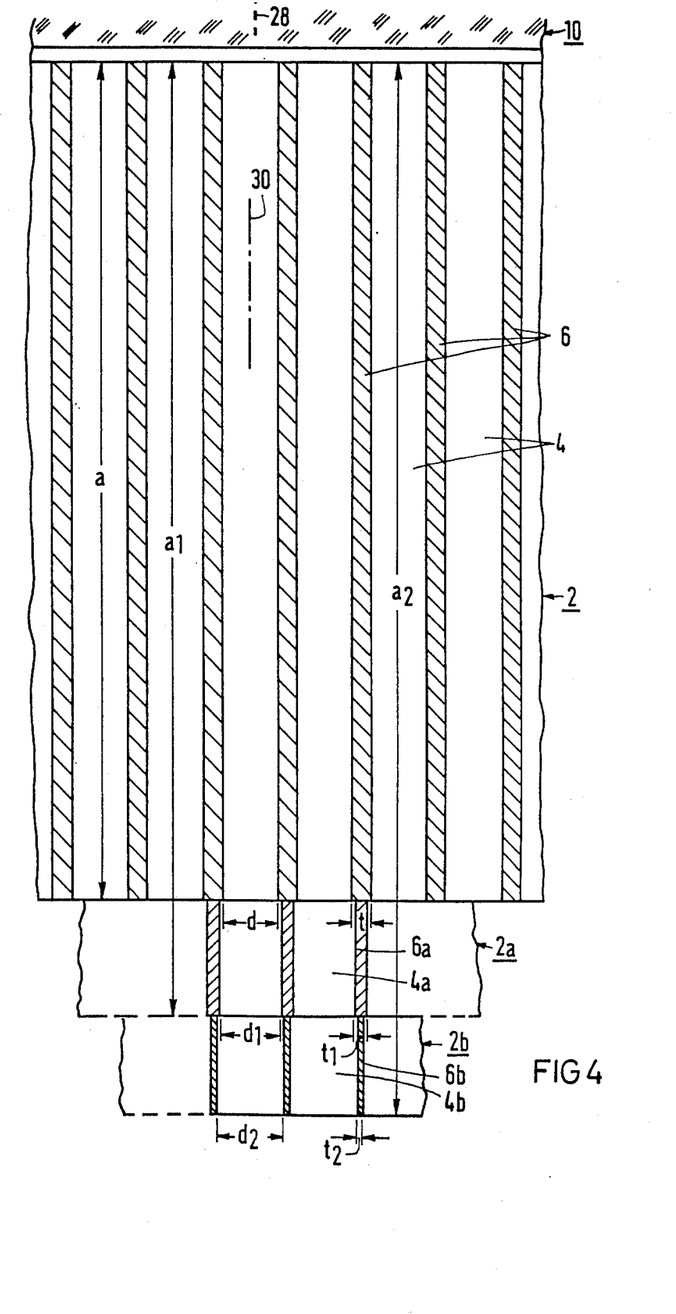
FIG. 4 shows comparable cross-sectional views of three different collimators for use in conjunction with a scintillation crystal device according to FIG. 1.

Collimators for lower range gamma energies may be designed by varying the septa thickness (hole width) and length; the number of collimator channels 4 and their arrangement should be the same for all collimator types, equaling the number and arrangement of the crystal teeth 20. As pointed out, the shape of the collimator channels 4 may be squared, i.e. in correspondence with the cross-sectional shape of the crystal teeth 20. Three types of collimators 2, 2a, 2b may be designed for the camera, as depicted schematically in FIG. 4. All three collimators 2, 2a, 2b of FIG. 4 are proportionally sized, the shortest one drawn in full lines ("basic" collimator 2), covering the photon energy span from 270–360 KeV (67-Ga, 131-I) and having the characteristics and dimensions given in FIG. 1. The second collimator 2a is longer and has thinner septa 6a. Its energy ranges from 190–270 KeV (111-In, 195-Au, 75-Se). The longest collimator 2b with the thinnest septa 6b is designed for energies ranging from 150–190 KeV (123-I, 67-Cu, 81 m-Kr). The axis 30 of each collimator channel 4, 4a, 4b is strictly aligned with the axis 28 of a particular crystal tooth 20. In FIG. 4, the two longer collimators 2a, 2b having decreasingly thinner septa 6a, 6b are shown only at their lower "visible" parts. The superimposed drawing emphasizes the retained alignment of the crystal teeth and collimator channel axes 28 and 30, respectively.

Figure 5:
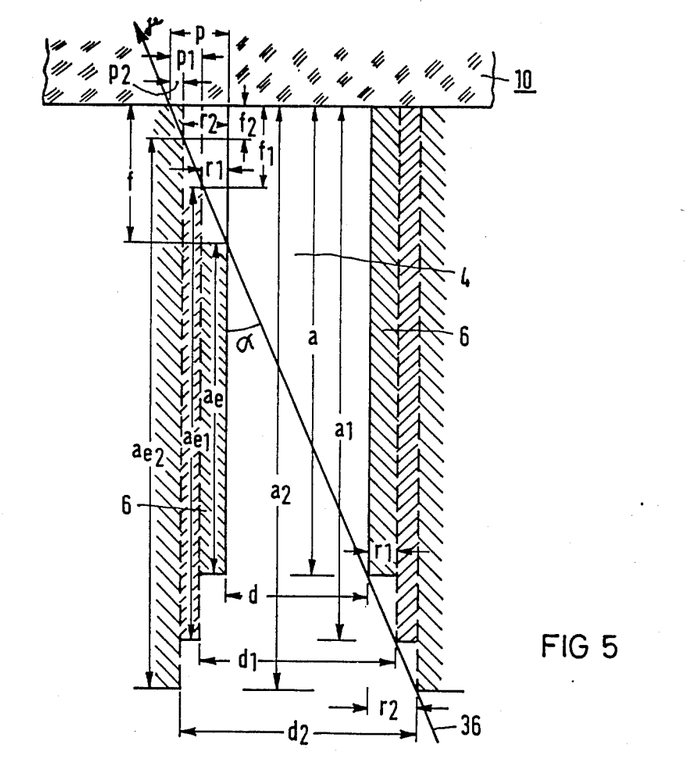
FIG. 5 shows the principle in the design of a series of collimators for application in a scintillation camera according to the invention.

FIG. 5 illustrates the principle of designing collimators for lower gamma energy ranges, after the "basic" collimator 2 has been designed. In FIG. 5, reference characters without any index stand for the "basic" collimator 2. An index "1" stands for a 270 KeV collimator 2a, and an index "2" stands for a 190 KeV collimator 2b. The diagonal full line 36 indicates the gamma ray direction through the "basic" 364 KeV collimator 2, the slope of which ($tg\alpha$) is determined by f with $f = 2\mu^{-1}$, and the continuation of which in the crystal 10 determines the shape of a crystal pyramid tooth 20. By knowing $f_1$ and $f_2$, the values for the collimators 2a and 2b for 270 and 190 KeV, respectively, one can derive the $r_1$ and $r_2$ values (provided the slope is retained), which give the maximum "displacement" values from a to $a_1$ and $a_2$ and from d to $d_1$ and $d_2$, thus, from t to $t_1$ and $t_2$, since the collimator channel axis remains the same. From the following geometric relations $$d/a_e = p/f = p_1/f_1 = p_2/f_2 = r_1/(f-f_1) = r_2/(f-f_2),$$

one can define $r_1$ (or $r_2$):

$$r_{1(2)} = d(f-f_{1(2)})/a_e. \quad (10)$$

Based on the same geometric relations, one can derive the following equations:

$$a_{1(2)} = a + (f - f_{1(2)}) \quad (11)$$

$$d_{1(2)} = d + 2r_{1(2)} \quad (12)$$

$$t_{1(2)} = t - 2r_{1(2)} \quad (13)$$

Parameter values calculated on the basis of equations (10), (11), (12) and (13) were: $a_1 = 54.398$ mm;

$d_1 = 3.91818$ mm; and $t_1 = 0.68182$ mm, for the 270 KeV collimator 2a; and $a_2 = 55.81$ mm; $d_2 = 4.133$ mm; and $t_2 = 0.466$ mm; for the 190 KeV collimator 2b. These parameter values were rounded; the rounded parameter values were subsequently "adjusted" to provide an adequate geometric efficiency E and, in particular, geometric resolution R (as will be explained later). The calculated (rounded) "calc." values and the adjusted "adjust." values of the essential parameters for the 270 and 190 KeV collimators 2a and 2b, respectively, are represented in Table V:

TABLE V

| Gamma energy (max. KeV) | a calc. (mm) | a adjust. (mm) | d cal. (mm) | d adj. (mm) | t cal. (mm) | t adj. (mm) | d + t cal. (mm) | d + t adj. (mm) |
|---|---|---|---|---|---|---|---|---|
| 270 | 54 | 56 | 3.9 | 3.8 | 0.7 | 0.8 | 4.6 | 4.6 |
| 190 | 56 | 60 | 4.1 | 4.0 | 0.5 | 0.6 | 4.6 | 4.6 |

Based on geometric relations derived from FIGS. 1 and 3, the collimator d and a parameters may be expressed as follows:

$$d = (n - 2t)(a - f)/(a - 2h - 3f) \quad (14)$$

$$a = f - ((2d(f + h))/(n - d - 2t)) \quad (15)$$

These are useful equations for theoretical crosscheckings of the design. Also, for predicting the collimator performance when designing it, the parameter a can be expressed in terms of parameters derived from Anger formulas (7) and (8) for the geometric efficiency E:

$$a = (10^3 K d^2 / \sqrt{E} (d + t)) + 2\mu^{-1} \quad (16)$$

or for the geometric resolution R:

$$a = (d(b + c)/(R - d)) + 2\mu^{-1} \quad (17)$$

Radionuclides having gamma ray energies up to 140 KeV may be imaged with conventional low energy collimators, due to an almost complete absorption of low energy gamma rays up to 100 KeV within a conventional crystal thickness layer or base 22 of ¼" (and in particular of ⅜"), i.e. beneath the newly designed crystal teeth 20.

(c) Summarized Strategy of Camera Head Design

From the above considerations, the strategy in the design of a scintillation camera may be summarized as followings:

Design of the "basic" collimator (e.g. made of tantalum). This is done for the highest gamma photon energy the camera is planned for (364 KeV, in this case). The preliminary design, which is to be done according to the characteristics of the similar collimator used with a conventional single crystal scintillation camera (Siemens, 364 KeV, in this case), should be adjusted to the camera concept together with the crystal-light guide complex design, with some reduction of its length and narrowing of its apertures, but still to retain similar geometric efficiency and geometric resolution of the (particular) conventional collimator; thus, the design of two collimators for lower energies (for 270 KeV and for 190 KeV, also made of tantalum) is "prepared", which should both have better geometric efficiencies and geometric resolutions as compared to the "basic" collimator.

Design of the crystal-light guide complex. This is done according to the "basic" collimator, as stressed above. Actually, mutual readjustments of both, crystal-light guide complex design and preliminary design of the "basic" collimator should be done, by meeting the following requirements: f to be $2\mu^{-1}$ for 364 KeV in Ta; h to be not less than 1"; n to be not less than 0.8 mm; and as to the collimator parameters: a to be shorter, and d to be narrower than the same parameters at the conventional (Siemens) design; E and R to retain the values of the similar conventional (Siemens) collimator.

Design of collimators for 270 KeV and 190 KeV gamma photons (also made of tantalum). The preliminary design of these collimators should be done on the basis of equation (10), evaluating parameters $p_1$ and $p_2$, assuming that the specific slope, $tg\alpha$, is retained. Then, final designs with slopes done according to the respective f values (which should give the relevant $tg\alpha_1$ and $tg\alpha_2$, both larger than $tg\alpha$), should evaluate $a_1$, $d_1$ and $t_1$ as well as $a_2$, $d_2$ and $t_2$, according to equations (11), (12), and (13). At any rate, the final versions, with "rounded" and then "adjusted" values for $a_1$, $d_1$, $t_1$, and $a_2$, $d_2$, $t_2$, will have better $E_1$ and $R_1$ values, as well as better $E_2$ and $R_2$ values, as compared to the E and R values. Also in this case, the indexes "1" and "2" are assigned to parameters characteristic for a 270 KeV and 190 KeV collimator, respectively.

Theoretical Considerations

Anger formulas (7) and (8) for E and R, respectively, have been used for theoretical testing of the collimator performance designed according to the present invention.

The calculated geometric efficiencies E (acc. to equation 7) of the collimators designed for maximum 360, 270 and 190 KeV energies were: 254, 278 and 282, respectively. The calculated geometric resolutions R (acc. to equation 8) of the same collimators, i.e. for maximum 360, 270 and 190 KeV energies at a 10 cm distance were 11.3, 11.2 and 11.1 mm of the geometric FWHM, respectively.

As stated above, low energy collimators designed for conventional single crystal scintillation cameras with known performance characteristics may be used with the present design for gamma photon energies up to 140 KeV.

Means for a theoretical prediction of the sensitivity gain of the new crystal design has been developed, too. The crystal sensitivity can be considered as being a function of the crystal volume and of the absorption rate of particular gamma ray energies in it. A parameter, including both volumetric and photon absorption factors, has been used for the prediction of sensitivity gain of the present crystal design as compared with the conventional scintillation crystal thickness of e.g. ¼".

One collimator channel in the present design relatively strictly "controls" one particular portion of the crystal 10, including a portion having conventional crystal thickness and a portion represented by a crystal tooth on top thereof. Such a situation can be used for specifying the effective portion of the new crystal design "seen" by a single collimator channel 4 as a "crystal unit". Thus, a comparison for volumetric and photon absorption gain between the conventional and new crystal design can be made within a representative crystal unit, the integrated effect over a total number of crystal units (equaling the number of collimator channels) giving a good approximation of the overall sensitivity ratio of the two crystal parts.

Volumetric Gain

Figure 6A:
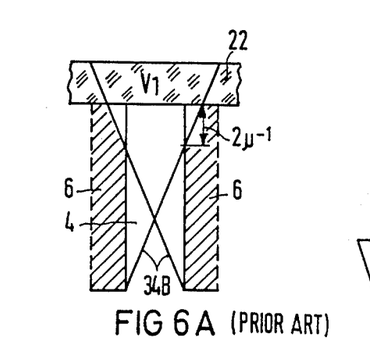
FIG. 6 shows a two-dimensional scheme of a volumetric principle used for calculating the sensitivity gain of the new scintillation crystal device.
Figure 6B:
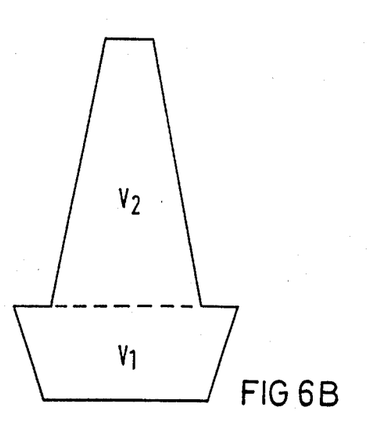

A two-dimensional presentation of the crystal unit, comprising a volume portion $V_1$ "belonging" to the conventional crystal thickness, and a volume portion $V_2$ belonging to the new design, i.e. to a crystal "tooth" is illustrated in FIG. 6B.

FIG. 6A illustrates the principle of determining the $V_1$ volume of a crystal unit; this volume $V_1$ represents a quadrilateral truncated pyramid, with its borderline sides determined by the continuation of gamma ray directions 34B penetrating at both inner ends of a particular collimator channel 4 at a distance $2\mu^{-1}$ (i.e. f) from the end of the septum 6. The two bases of the $V_1$ pyramid are limited by the face ends of the plate 22 having the conventional crystal thickness s ($\frac{1}{4}''$, in this case).

Figure 7A:
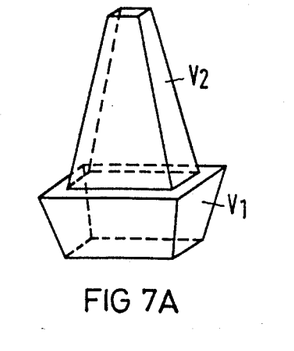
FIG. 7 illustrates a crystal sensitivity gain calculation principle based on volumetry and integration of an exponential gamma photon attenuation function.

FIG. 7A illustrates a three-dimensional presentation of the two volume parts $V_1$ and $V_2$ of the crystal unit which was two-dimensionally shown in FIG. 6B.

Both $V_1$ and $V_2$ volumes can be calculated on the basis of the known equation (18) for a truncated pyramid volume V:

$$V = H(B_1 + \sqrt{B_1 B_2} + B_2)/3, \quad (18)$$

where H respresents the pyramid height and $B_1$ and $B_2$ represent its larger and smaller bases, respectively. In order to obtain a deeper insight in the sensitivity gain of the present crystal 10, theoretical test for various gamma ray energies were done against the "basic" collimator for 364 KeV (dimensions are given in Table IV), and for collimators for 270 and 190 KeV ("adjust" dimensions are given in Table V). Then, the penetration factor $f(=2\mu^{-1})$ was varied as a function of energy: By varying is for 360, 270, 190 and 140 KeV photon energies, different $V_1$ volumes were obtained; volume $V_2$, as designed for 360 KeV, was kept the same throughout theoretical testing. In other words, various energy dependent $V_1$ volumes of a "crystal unit" were determined against the same $V_2$ volume being dependent on 360 KeV gamma rays.

Based on geometric relations given in FIG. 3, one obtains:

$$d/a_c = p/2\mu^{-1} = p_3/(s + c_1 + 2\mu^{-1}),$$

where $f = 2M^{-1}$.

One can derive thereof the following equations to be used for calculating the volumetric gain:

$$p = d2\mu^{-1}/a_c \quad (19)$$

$$p_3 = d(s + c_1 + 2\mu^{-1})/a_c \quad (20)$$

The $V_1$ volume is given by:

$$V_1 = s(B_1 + \sqrt{B_1 B_2} + B_2)/3, \quad (21)$$

where the meanings and values of d, $a_e$ und s are as given in Table IV; the $B_1$ and $B_2$ bases are given by:

$$B_1 = (d + 2p_3)^2 \quad (22)$$

$$B_2 = (d + 2p)^2 \quad (23)$$

Volume $V_2$ is given by:

$$V_2 = (h - s)(B_3 + \sqrt{B_3 B_4} + B_4)/3, \quad (24)$$

with $B_3$ (larger) and $B_4$ (smaller) bases being given by:

$$B_3 = ((2t + d) - (2p_3))^2 \quad (25)$$

$$B_4 = n^2 \quad (26)$$

where the meanings and values for h, s, t, d and n are given in Table IV, and for f in Table III, where n is obtained by equation (6), where p is obtained by equation (19), and where $p_3$ is obtained by equation (20).

Calculations basedon the above formulas and quoted values provide the results as given in Table VI:

TABLE VI

| Energy range (max. KeV) | Calculated parameters | | | |
|---|---|---|---|---|
| | p(mm) | $p_3$(mm) | $B_1$(mm$^2$) | $B_2$(mm$^2$) |
| 360 | 0.488 | 1.033 | 29.877 | 19.149 |
| 270 | 0.215 | 0.728 | 27.625 | 17.893 |
| 190 | 0.1095 | 0.599 | 27.019 | 17.799 |
| 140 | 0.049 | 0.532 | 25.644 | 16.794 |
| Energy range (max. KeV) | Calculated parameters | | | |
| | $V_1$(mm$^3$) | $B_3$(mm$^2$) | $B_4$(mm$^2$) | $V_2$(mm$^3$) |
| 360 | 154.40 | 13.943 | 0.689 | 112.592 |
| 270 | 143.406 | 13.943 | 0.689 | 112.592 |
| 190 | 141.181 | 13.943 | 0.689 | 112.592 |
| 140 | 133.752 | 13.943 | 0.689 | 112.592 |

(Parameter characteristics for the $V_2$ volume, which is dependent on a 360 KeV design, remain the same for all of the lower energies. The 140 KeV values concern the use of a 190 KeV tantalum collimator).

Photon Absorption Gain

Figure 7B:
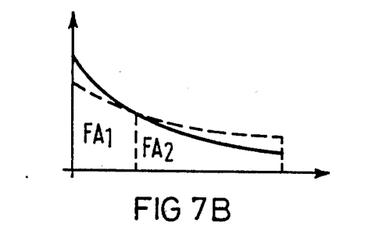

FIG. 7B presents a graph of an exponential absorption function of particular gamma photon energies in a crystal, wherein portion $FA_1$ shows the absorption in the $V_1$ volume, and portion $FA_2$ shows the absorption in the $V_2$ volume. The curve given in dashed lines, which approximates a photon energy higher than the curve given in full line, indicates in volume $V_2$ a greater absorption of high energy photons than of low photons.

Calculations of the absorption effect for determining the sensitivity ratio of the two crystal designs within a crystal unit are based on the following formulas, considering the integration of an exponential absorption function of a particular gamma ray energy in NaI. In order to calculate an activity fraction $F_A$ within the particular distance limits D=x and D=y, an exponential absorption function:

$$A_D = A_0 e^{-\mu D} \quad (27)$$

where $A_0$—activity at reference zero distance;
$A_D$—activity at distance D;
e—base of natural logarithm;
D—distance from reference zero point;
$\mu$—linear absorption coefficient of a particular gamma ray energy in NaI;

may be integrated by a definite integral (Bosnjakovic et al., "Radioaktive Isotope in Klinik und Forschung", Egermann, Vienna, 16, 2 (1984), p. 781:

$$F_A = A_{(x,y)} = \int_{D=x}^{D=y} A_0 e^{-\mu D} dD \qquad (28)$$

If the activity at reference zero distance $A_O$ is taken as a constant, then:

$$A_{(x,y)} = A_0 \int_{D=x}^{D=y} e^{-\mu D} dD, \int \text{ where for } A_0 = \qquad (29)$$

1 one obtains $\int F_A = \int_{D=x}^{D=y} e^{-\mu D} dD$

Such an integral has a very practical value $$F_A = (e^{-x\mu} - e^{-y\mu})/\mu \qquad (30)$$

leaving for calculations only the distance limits D=x and D=y between which the desired activity fraction $F_A$ has to be calculated.

Thus, the relative activity fractions $F_{A1}$ and $F_{A2}$ within the $V_1$ and $V_2$ volumes of a "crystal unit", respectively, can be calculated where the reference zero distance is at the inner collimator end (aluminium can). Then, using equation (30), $FA_1$ is integrated between the limits x=0 and y=s (=6.35 mm), while $FA_2$ integrated between x=s and y=h (=25.4 mm). The $\mu$ values for particular gamma photon energies and NaI material, as used for computations, are given in Table III.

The values for relative activity fractions absorbed within a NaI crystal unit, being functions of gamma photon energies and as computed according to equation (30), are given in Table VII:

TABLE VII

| Energy range max. KeV) | $FA_1$ | $FA_1$ % | $FA_2$ | $FA_2$ % | $\cdot$ AT ($FA_1 + FA_2$) | AT % |
|---|---|---|---|---|---|---|
| 360 | 0.5934 | 30.3 | 1.3625 | 69.7 | 1.9559 | 100 |
| 270 | 0.5598 | 35.3 | 1.0264 | 64.7 | 1.5862 | 100 |
| 190 | 0.4837 | 48.4 | 0.5145 | 51.6 | 0.9982 | 100 |
| 140 | 0.3420 | 75.5 | 0.1107 | 24.5 | 0.4527 | 100 |

Present Crystal Sensitivity Gain (SG)

Based on the product of the data obtained for volumetric absorption gain (Table VI) and for photon absorption gain (Table VII), one can obtain a very indicative insight into the sensitivity gain of the new crystal design. The volumetric gain for the two parts of the crystal unit will be given with a volume ratio, $V_2/V_1$; in the same way, gamma photon absorption gain will be given with an absorbed activity fraction ratio $FA_2/FA_1$. The sensitivity ratio for the two parts of the crystal unit will then be given with $S_2/S_1$, where:

$$S_2/S_1 = (V_2/V_1)(FA_2/FA_1)$$

and $$S_1 = 1 \qquad (31)$$

Then, the SG data can be evaluated as given in Table VIII, where:

$$SG = ST/S_1 = (S_2 + S_1)/S_1 \qquad (32)$$

which is realistic, since the "conventional portion" of $\frac{1}{4}''$ thickness of the crystal (crystal unit) is "in function".

TABLE VIII

| Energy range (max. KeV) | $V_2/V_1$ | $FA_2/FA_1$ | $S_2/S_1$ frac. | $S_2/S_1$ % | SG ($ST/S_1$) |
|---|---|---|---|---|---|
| 360 | 0.729 | 2.296 | 1.674 | 167.4 | 2.674 |
| 270 | 0.785 | 1.833 | 1.439 | 143.9 | 2.439 |
| 190 | 0.797 | 1.063 | 0.847 | 84.7 | 1.847 |
| 140 | 0.842 | 0.323 | 0.272 | 27.2 | 1.272 |

(The 140 KeV values concern the use of a 190 KeV Ta collimator)

It should be emphasized that the crystal sensitivity data of the new crystal device are presented here, and not the overall sensitivity (efficiency) data. For the latter ones, one should incoporate the collimator(s) data, which are not readily comparable for the conventional and the new design, due to the difference in energy ranges they are designed for, due the number of collimator channels, etc.

Problems associated with the new design may be those arising from an unusually interrelated arrangement of two materials of particular characteristics, namely a NaI crystal 10 and a light-guide 12 of window glass (e.g. quartz). Light refraction, temperature tolerance and manufacturing of the complex require special considerations.

Light Refraction

One of the characteristics of the light guide material should be its close similarity in the light refraction index of the crystal 10, i.e. of NaI. Adequate optical coupling is provided to prevent a mispositioning of scintillation events. Slight changes in light photon directions due to refraction can be neglected in a conventional scintillation camera design, where light photons have only one "chance" to be refracted. However, the present design gives a "multiple chance" to the light photons to be refracted, before they can serve the positioning task. Does such a "chance" produce an unacceptable effect in the positioning of events, and even more, in the sensitivity loss due to the fact that a significant percentage of the emitted light might miss the photomultiplier tubes?

Figure 8:
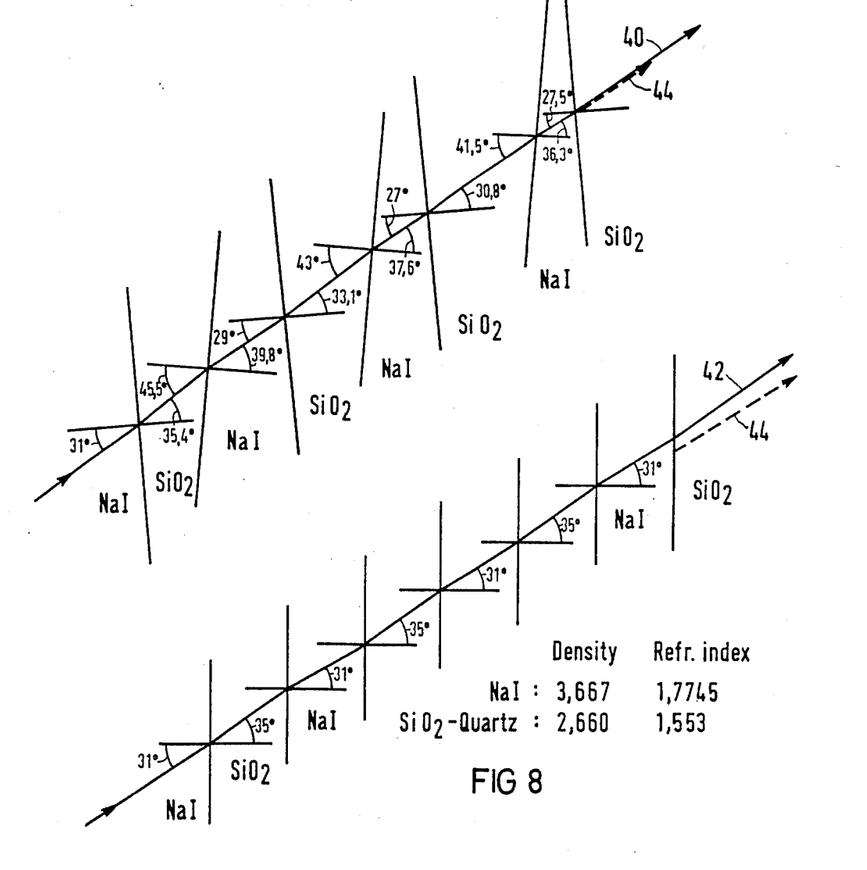
FIG. 8 illustrates a theoretical prediction of a light photon path through successively interposed layers of two slightly different light refracting materials such as NaI and Quartz.

A theoretical insight into this problem is obtainable by a "graphical experiment", as shown in FIG. 8. Quartz ($SiO_2$) is taken as the light guide material. The densities of NaI and $SiO_2$ and 3.67 and 2.66 g/cm$^3$, respectively; the refraction indices for the two materials (for sodium light, $\lambda = 589.3$ m$\mu$) are 1.7745 and 1.553, respectively. By knowing the fact that the light when passing from an optically less dense to a more dense material refracts towards a vertical (to a coupling borderline), and vice versa, one can test a light photon direction (path) for the passage through a series of successively arranged layers of NaI and $SiO_2$. The testing is done by multiplying the input or inlet angle (to the vertical to borderline) value (in degrees) by the ratio of the refraction indices of the two materials, to obtain the outlet angle value; the inlet angle value is multiplied by the ratio 1.7745/1.553 for the passage from NaI to SiO$_2$, and by 1.553/1.7745 for the passage from SiO$_2$ to NaI. FIG. 8 (top) illustrates a light photon passage 40 through an arrangement according to the present design, i.e. of NaI teeth 20 and interposed SiO$_2$ "negative teeth". For comparison reasons, FIG. 8 (bottom) provides a light photon passage 42 through a simple array of vertically parallel layers of the two materials. In both instances, two conditions are present: (a) in a plane perpendicular to that of the drawing, it is assumed that a light photon direction is strictly identical to the x or y coordinate axis, passing through the vertical midplanes of either NaI pyramids or an array of simple squared vertical layers of two materials; and (b) the starting angle of a light photon (generated in NaI) relative to the first vertical line (to a borderline between the materials) is 31°.

Tracing the light path 42 through the arrangement shown in FIG. 8 (bottom) is relatively simple, since only two angles, according to the two refraction index ratios, keep on changing at the parallel vertical borderlines of the two materials.

The tracing of the light path 40 of interest for the present design (FIG. 8, top) shows that changes of the angles occur, not only according to the refraction index ratios of the two materials, but also to the changing verticals of the borderlines.

The final result of this "experiment" (as compared to the light photon directions 44 with no refraction, whose starting directions in NaI are the same and whose end portions are shown in dashed lines) indicates this: a light photon passing through a simple vertical array of the two materials (FIG. 8, bottom) is more turned off from the starting direction than a light photon passing through an array of the present invention (FIG. 8, top). The present crystal device 10, 12 serves as a kind of "rectifier" for slightly different refraction indices of the two chosen materials NaI and SiO$_2$.

Temperature Tolerance

The present arrangement of NaI and SiO$_2$ interleaves the two materials, which differ in their temperature coefficients. In order to avoid stress cracking of the NaI crystal, which might even occur within the limited temperature range from 55° to 80° F., an adequate temperature shielding (thermoinsulation) of the appropriate portion of camera head should be provided.

Manufacturing Details

There is no problem in manufacturing tantalum collimators. They can easily be fabricated from commercially available tantalum tubes (Swann et al., J. Nucl. Med. 17, 1, 51, (1976); Kircos et al., J. Nucl. Med. 19, 3, 322 (1978)). For the present application, several practical solutions exist for making the collimator channels to adopt a square cross-section. One of them is that Ta tubes, with walls thick one half of the designed collimator septum thickness, may be made squared; by sticking them together side by side, an array of square collimator channels can be obtained. Another solution is to make square-waved Ta plates, of thickness equaling that of collimator septa; sides of square-waves should equal those of cross-section sides of collimator channels; length of the plate should match the diameter of collimator and height of the plate should equal the length (thickness) of collimator. By sticking such Ta plates together at the corner sites of square-waves, one can fabricate the basis for the production of either square-shaped collimators or for "peeling out" circle-shaped collimators.

Figure 9:
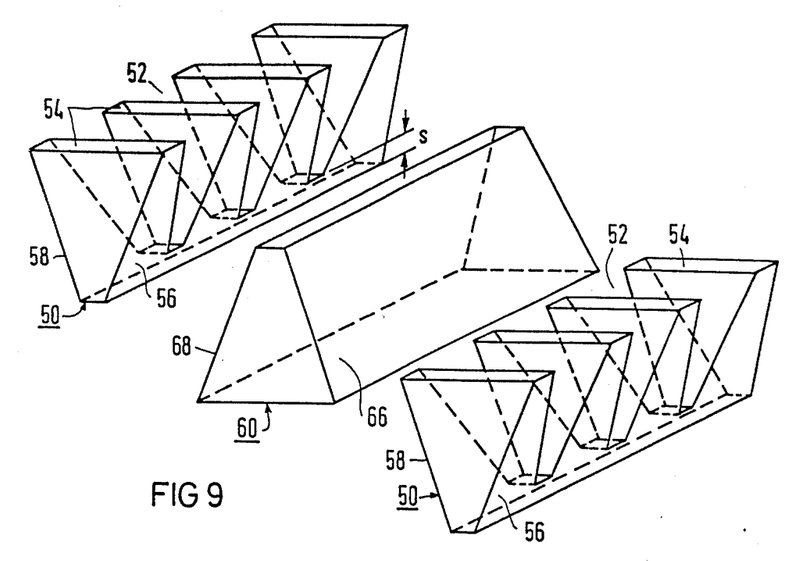
FIG. 9 illustrates a light-guide portion of a crystal-light-guide unit which can easily be manufactured.

The manufacture of the crystal-light guide complex is not a too complicated procedure. One of the solutions for manufacturing such complex is given in FIG. 9. Two types of specifically shaped bodies or rows 50, 60 of light guide material are provided. Rows 50 contain each quadrilateral truncated recesses 52 and protrusions 54 formed from an elongated pyramid of the light guide material. Their elongated sides 56, 58 form an angle smaller than 90° with each other. Rows 60 are simply shaped. They are also in the form of an elongated pyramid, and they are reversed with respect to rows 50. Rows 60 contain correspondingly elongated side walls 66, 68. If the sequential rows 50, 60 are optically stuck together, whereby wall 58 attaches wall 66, and wall 68 attaches wall 56, the formed recesses 52 are "filled" with adequately shaped truncated pyramids of NaI crystal, which are optically coupled. The crystal-light guide-complex can easily be made if the recesses 52 of the rows 50 are filled with truncated pyramids of NaI crystal (and optically coupled) first, and then rows 50, 60 are optically stuck together. The upper side of the thus formed block, with the exposed bases of crystal pyramids, will then be optically coupled to the crystal layer or base 22 of conventional thickness s, and the other side of the block is coupled to the photomultiplier tubes. Also, the other side of the block may be coupled to a thin layer of window glass 70 (see FIG. 10) which is to be coupled to the photomultiplier tubes 14, in a solution providing for an exchangeable camera head design.

Exchangeable Head Design

Figure 10:
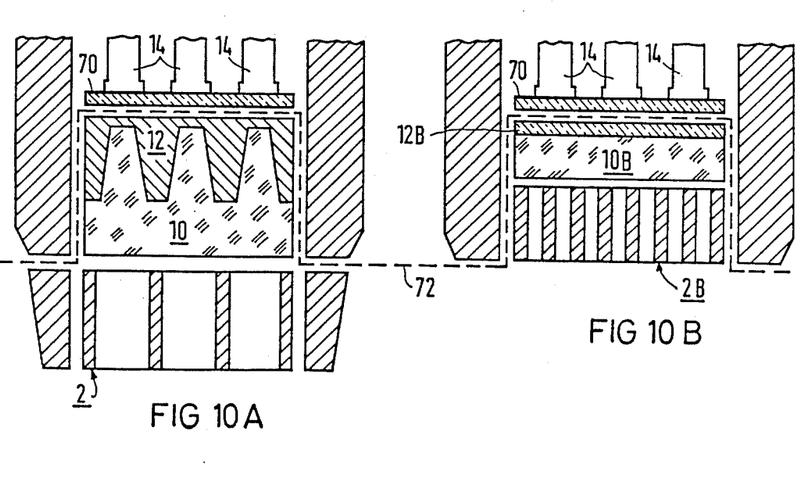
FIG. 10 shows a portion of a single crystal scintillation camera having two types of exchangeable heads: one designed according to the present invention and the other being of conventional design.

A solution which retains fine spatial resolution at static imaging for low gamma energies is illustrated in FIG. 10. This solution provides for a scintillation camera with exchangeable crystal-light guide collimator complexes 2, 10, 12 and 2B, 10B, 12B, respectively, at the level of dashed lines 72. FIG. 10A represents the proposed new camera design concept, and FIG. 10B represents a modality B switched over to the conventional camera design. The interchangeable optical surfaces are located in the light guide portion 12 and 12B. Such a "non-trade-off" solution meets all requirements in scintillation camera performance (including SPECT) and is still effective.

Advantages

The new design meets the requirements of modern trends in nuclear medicine for evaluating dynamics, quantisation and biochemistry in vivo. It is primarily designed for physiologic imaging, where high temporal resolution and efficiency for medium energy gamma photons are required, like in "first pass" dynamic cardiac studies (including those with 99 m-Tc), in detection of new short lived single photon emitting tracers, in SPECT, in PET with a dual head camera configuration.

What is claimed is:
1. A scintillation crystal device for application in a scintillation camera, comprising
   (a) a crystal base having a first end for receiving radiation, and a second end opposite to said first end; and
   (b) a plurality of crystal teeth in the form of truncated pyramids, said teeth being arranged on said second end of said crystal base.

2. The scintillation crystal device in accordance with claim 1, wherein said pyramids are quadrilateral.

3. The scintillation crystal device in accordance with claim 1, wherein said pyramids are arranged in a regular pattern on said second end of said crystal base.

4. The scintillation crystal device in accordance with claim 1, wherein the space between said crystal teeth is filled with a light guide material.

5. The scintillation crystal device in accordance with claim 4, wherein said light guide material extends beyond the full height of said crystal teeth, said light guide material thus covering said teeth and forming a plane surface for emitting light therefrom.

6. The scintillation crystal device in accordance with claim 5, wherein said crystal base and said crystal teeth comprise sodium iodide, and wherein said light guide comprises a quartz glass.

7. The scintillation crystal device in accordance with claim 1, wherein said crystal teeth are positioned in respective recesses of at least one body formed of a light guide material.

8. The scintillation crystal device in accordance with claim 7, wherein said body is formed as an elongated pyramid and contains a plurality of said recesses and of protrusions, and wherein said body is positioned adjacent to a further body formed of a light guide material, said further body being formed as an elongated continuous pyramid.

9. In a scintillation camera comprising (a) a collimator having a plurality of parallel channels for receiving and for transmitting radiation therethrough, (b) a predetermined number of photomultipliers arranged in an array, and (c) a scintillation crystal device disposed between said collimator and said photomultiplier array, the improvement wherein said scintillation crystal device comprises (d) a crystal base having a first end for receiving radiation transmitted through said collimator channels, and a second end opposite to said first end; and (e) a plurality of crystal teeth in the form of truncated pyramids having parallel longitudinal axes, said teeth being arranged on said second end of said crystal base such that said longitudinal axes of said pyramids are aligned with the longitudinal axes of said collimator channels.

10. The scintillation camera according to claim 9, wherein said pyramids are quadrilateral, and wherein said collimator channels have a rectangular cross section.

11. The scintillation camera according to claim 9, wherein the space between said crystal teeth is filled with a material for guiding light, said light being generated when radiation transmitted through said collimator channels impinges on said crystal base and said crystal teeth.

12. The scintillation camera according to claim 11, wherein said light guiding material extends beyond the full height of said crystal teeth, said light guiding material thereby covering said crystal teeth, and wherein said light guiding material forms a plane surface for attaching said photomultipliers thereto.

13. The scintillation camera in accordance with claim 9, wherein said collimator channels are of a squared configuration.

* * * * *